United States Patent
Akcakaya et al.

(10) Patent No.: US 12,106,401 B2
(45) Date of Patent: Oct. 1, 2024

(54) SYSTEMS AND METHODS FOR TRAINING MACHINE LEARNING ALGORITHMS FOR INVERSE PROBLEMS WITHOUT FULLY SAMPLED REFERENCE DATA

(71) Applicant: REGENTS OF THE UNIVERSITY OF MINNESOTA, Minneapolis, MN (US)

(72) Inventors: Mehmet Akcakaya, Minneapolis, MN (US); Burhaneddin Yaman, Minneapolis, MN (US); Seyed Amir Hossein Hosseini, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 695 days.

(21) Appl. No.: 17/075,411

(22) Filed: Oct. 20, 2020

(65) Prior Publication Data
US 2021/0118200 A1   Apr. 22, 2021

Related U.S. Application Data

(60) Provisional application No. 62/923,763, filed on Oct. 21, 2019.

(51) Int. Cl.
| | | |
|---|---|---|
| *G06T 11/00* | (2006.01) | |
| *G06N 3/04* | (2023.01) | |
| *G06N 3/08* | (2023.01) | |
| *G16H 30/40* | (2018.01) | |

(52) U.S. Cl.
CPC .............. *G06T 11/005* (2013.01); *G06N 3/04* (2013.01); *G06N 3/08* (2013.01); *G16H 30/40* (2018.01)

(58) Field of Classification Search
CPC ..... G06T 11/005; G06T 7/0012; G16H 30/40; G16H 50/70; G06N 3/04; G06N 3/08; G06N 3/045; G06N 3/047
See application file for complete search history.

(56) References Cited

U.S. PATENT DOCUMENTS

| | | | |
|---|---|---|---|
| 9,297,873 B2* | 3/2016 | Block | G01R 33/5611 |
| 10,712,416 B1* | 7/2020 | Sandino | G16H 30/40 |
| 2017/0053402 A1* | 2/2017 | Migukin | G06T 7/0012 |
| 2019/0257905 A1* | 8/2019 | Cheng | G01R 33/5608 |

(Continued)

OTHER PUBLICATIONS

Cheng, J., Wang, H., Ying, L., Liang, D. (2019). Model Learning: Primal Dual Networks for Fast MR Imaging. In: , et al. Medical Image Computing and Computer Assisted Intervention—MICCAI 2019. MICCAI 2019. Lecture Notes in Computer Science(), vol. 11766. Springer, Cham (Year: 2019).*

(Continued)

*Primary Examiner* — Qian Yang
(74) *Attorney, Agent, or Firm* — QUARLES & BRADY LLP

(57) ABSTRACT

Self-supervised training of machine learning ("ML") algorithms for reconstruction in inverse problems are described. These techniques do not require fully sampled training data. As an example, a physics-based ML reconstruction can be trained without requiring fully-sampled training data. In this way, such ML-based reconstruction algorithms can be trained on existing databases of undersampled images or in a scan-specific manner.

28 Claims, 6 Drawing Sheets

(56) References Cited

U.S. PATENT DOCUMENTS

| | | | | |
|---|---|---|---|---|
| 2019/0385047 | A1* | 12/2019 | Lei | G06F 30/27 |
| 2020/0090036 | A1* | 3/2020 | Nakata | G06N 3/084 |
| 2020/0311541 | A1* | 10/2020 | Cmielowski | G06N 3/04 |
| 2020/0311878 | A1* | 10/2020 | Matsuura | G06V 10/82 |
| 2022/0130017 | A1* | 4/2022 | Zhang | A61B 5/7267 |

OTHER PUBLICATIONS

Aggarwal, Hemant K., Merry P. Mani, and Mathews Jacob. "MoDL: Model-based deep learning architecture for inverse problems." IEEE transactions on medical imaging 38.2 (2018): 394-405. (Year: 2018).*

Hyun, Chang Min, et al. "Deep learning for undersampled MRI reconstruction." Physics in Medicine & Biology 63.13 (2018): 135007. (Year: 2018).*

Knoll, Florian, et al. "Deep learning methods for parallel magnetic resonance image reconstruction." arXiv preprint arXiv:1904.01112 (2019). (Year: 2019).*

Liang, Dong, et al. "Deep MRI reconstruction: unrolled optimization algorithms meet neural networks." arXiv preprint arXiv:1907.11711 (2019). (Year: 2019).*

Qin, Chen, et al. "Convolutional recurrent neural networks for dynamic MR image reconstruction." IEEE transactions on medical imaging 38.1 (2018): 280-290. (Year: 2018).*

Rueckert, Daniel, and Julia A. Schnabel. "Model-based and data-driven strategies in medical image computing." Proceedings of the IEEE 108.1 (2019): 110-124. (Year: 2019).*

Wu, Dufan, Kyungsang Kim, and Quanzheng Li. "Computationally efficient deep neural network for computed tomography image reconstruction." Medical physics 46.11 (2019): 4763-4776. (Year: 2019).*

Zhussip, Magauiya, Shakarim Soltanayev, and Se Young Chun. "Training deep learning based image denoisers from undersampled measurements without ground truth and without image prior." Proceedings of the IEEE/CVF Conference on Computer Vision and Pattern Recognition. 2019. (Year: 2019).*

Hammernik, Kerstin, et al. "Learning a variational network for reconstruction of accelerated MRI data." Magnetic resonance in medicine 79.6 (2018): 3055-3071.

Senouf, O., et al. "Self-supervised learning of inverse problem solvers in medical imaging." arXiv preprint arXiv:1905.09325 (2019).

Akcakaya M, Basha TA, Goddu B, Goepfert LA, Kissinger KV, Tarokh V, Manning WJ, Nezafat R. Low-dimensional-structure self-learning and thresholding: Regularization beyond compressed sensing for MRI Reconstruction. Magn Reson Med 2011;66(3):756-767.

Akcakaya M, Moeller S, Weingartner S, Ugurbil K. Scan-specific robust artificial-neural networks for k-space interpolation (RAKI) reconstruction: Database-free deep learning for fast imaging. Magn Reson Med 2019;81(1):439-453.

Akcakaya M, Nam S, Hu P, Moghari MH, Ngo LH, Tarokh V, Manning WJ, Nezafat R. Compressed sensing with wavelet domain dependencies for coronary MRI: a retrospective study. IEEE Trans Med Imaging 2011;30(5):1090-1099.

Dar Suh, Özbey M, Çatli AB, Çukur T. A Transfer-Learning Approach for Accelerated MRI Using Deep Neural Networks. Magn Reson Med 2020.

Han, Y. et al. "k-space deep learning for accelerated MRI," arXiv preprint arXiv:1805.03779 (2019).

Han, Y. et al. "Deep learning with domain adaptation for accelerated projection-reconstruction MR," arXiv preprint arXiv:1703.01135 (2018).

Hosseini SAH, et al. "Accelerated coronary MRI using 3D SPIRiT-RAKI with sparsity regularization," in Proc. IEEE ISBI, 2019, pp. 1692-1695.

Hosseini SAH, et al. "Accelerated coronary MRI with sRAKI: a database-free self-consistent neural network k-space reconstruction for arbitrary undersampling," PLoS ONE, 2020, 15(2):e0229418.

Hosseini SAH, et al. "sRAKI-RNN: accelerated MRI with scan-specific recurrent neural networks using densely connected blocks," in SPIE Wavelets and Sparsity XVIII, 2019, p. 111381B.

Hosseini SAH, et al. Dense Recurrent Neural Networks for Accelerated MRI: History-Cognizant Unrolling of Optimization Algorithms. arXiv preprint arXiv:1912.07197 (2020).

Kim, T. et al. "LORAKI: Autocalibrated Recurrent Neural Networks for Autoregressive MRI Reconstruction in k-Space," arXiv preprint arXiv:1904.09390 (2019).

Knoll, F., et al. "Advancing machine learning for MR image reconstruction with an open competition: Overview of the 2019 fastMRI challenge," arXiv preprint arXiv:2001.02518 (2020).

Knoll, F., et al. "Deep-learning methods for parallel magnetic resonance imaging reconstruction: a survey of the current approaches, trends, and issues," IEEE Signal Processing Magazine, vol. 37, No. 1, pp. 128-140, 2020.

Kwon, K. et al. "A parallel MR imaging method using multilayer perceptron," Medical Physics, vol. 44, No. 12, pp. 6209-6224, 2017.

Lee, D. et al. "Deep residual learning for accelerated MRI using magnitude and phase networks," arXiv preprint arXiv:1804.00432 (2018).

Lei K, Mardani M, Pauly JM, Vasawanala SS. Wasserstein GANs for MR Imaging: from Paired to Unpaired Training. arXiv preprint arXiv:1910.07048 (2020).

Liang D, Cheng J, Ke Z, Ying L. Deep Magnetic Resonance Image Reconstruction: Inverse Problems Meet Neural Networks. IEEE Signal Processing Magazine, 2020, 37(1):141-151.

Schlemper, J. et al. "A deep cascade of convolutional neural networks for dynamic MR image reconstruction," IEEE Trans Med Imaging, vol. 37, No. 2, pp. 491-503, 2018.

Sim B, Oh G, Lim S, Ye JC. Optimal Transport, CycleGAN, and Penalized LS for Unsupervised Learning in Inverse Problems. arXiv preprint arXiv:1909.12116 (2019).

Wang, S. et al. "Accelerating magnetic resonance imaging via deep learning," in Proc IEEE ISBI, 2016, pp. 514-517.

Yaman B, Hosseini SAH, Akcakaya M. Noise2Inpaint: Learning Referenceless Denoising by Inpainting Unrolling. arXiv preprint arXiv:2006.09450 (2020).

Yaman B, Hosseini SAH, Moeller S, Ellermann J, Ugurbil K, Akcakaya M. Self-Supervised Learning of Physics-Guided Reconstruction Neural Networks Without Fully Sampled Reference Data. Magn Reson Med, 2020, 84(6):3172-3191.

Yaman B, Hosseini SAH, Moeller S, Ellermann J, Ugurbil K, Akcakaya M. Self-Supervised Physics-Based Deep Learning MRI Reconstruction Without Fully-Sampled Data. arXiv preprint arXiv:1910.09116 (2019).

* cited by examiner

SYSTEMS AND METHODS FOR TRAINING MACHINE LEARNING ALGORITHMS FOR INVERSE PROBLEMS WITHOUT FULLY SAMPLED REFERENCE DATA

CROSS-REFERENCE TO RELATED APPLICATIONS

This application claims the benefit of U.S. Provisional Patent Application Ser. No. 62/923,763, filed on Oct. 21, 2019, and entitled "SYSTEMS AND METHODS FOR TRAINING MACHINE LEARNING ALGORITHMS FOR INVERSE PROBLEMS WITHOUT FULLY SAMPLED REFERENCE DATA," which is herein incorporated by reference in its entirety.

STATEMENT REGARDING FEDERALLY SPONSORED RESEARCH

This invention was made with government support under HL111410 and EB027061 awarded by the National Institutes of Health. The government has certain rights in the invention.

BACKGROUND

Deep learning ("DL") has emerged as a tool for improving image reconstruction. A common strategy among DL methods is the physics-driven approach, where a regularized iterative algorithm alternating between data consistency and a regularizer is unrolled for a finite number of iterations. This unrolled network is then trained end-to-end in a supervised manner, using fully-sampled data as ground truth for the network output. However, in a number of scenarios, it is difficult to obtain fully-sampled datasets, due to physiological constraints such as organ motion or physical constraints such as signal decay.

SUMMARY OF THE DISCLOSURE

The present disclosure addresses the aforementioned drawbacks by providing a computer-implemented method for training a machine learning algorithm to reconstruct an image. The method includes accessing sub-sampled data with a computer system and dividing the sub-sampled data into a first data subset and a second data subset. A machine learning algorithm is trained by using the first data subset within the machine learning algorithm during training and using the second data subset in a loss function that is used during training. The trained machine learning algorithm is then stored in the computer system for later use.

It is another aspect of the present disclosure to provide a method for reconstructing an image from undersampled k-space data. A pre-trained neural network is accessed with a computer system. The pre-trained neural network has been trained on sub-sampled k-space data that were divided into a first k-space data subset and a second k-space data subset, where the pre-trained neural network was trained by using the first k-space data subset within the neural network during training and using the second k-space data subset in a loss function used during training. Undersampled k-space data are accessed with the computer system, where the undersampled k-space data were obtained from a subject using a magnetic resonance imaging ("MRI") system. The undersampled k-space data are input to the pre-trained neural network, generating output as a reconstructed image that depicts the subject. The reconstructed image is then displayed to a user using the computer system.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1A:
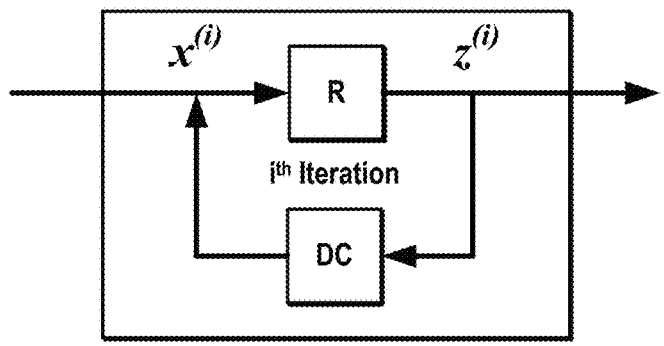
FIG. 1A shows a schematic example of an iterative scheme of a reconstruction problem.

Described here are systems and methods for self-supervised training of machine learning ("ML") algorithms for reconstruction in inverse problems, without requiring fully sampled training data. As an example, an ML algorithm may implement a physics-based ML reconstruction. As another example, the ML algorithm may implement a compressed sensing based reconstruction, or other inverse problems with transform domain sparsity regularization. The ML-based reconstruction algorithms described in the present disclosure can be trained on existing databases of undersampled images or in a scan-specific manner.

In general, the systems and methods described in the present disclosure divide an individual data set into training and loss criterion subsets based on sub-sampled data points. During training, data consistency is enforced over the training subset, while the loss criterion subset is used to define the loss function. In this way, ML algorithms can be trained for physics-driven inverse problem reconstruction in many settings, where fully-sampled data is not available or possible to acquire. As noted above, the ML algorithms can also be trained for other inverse problems, such as compressed sensing based reconstructions or other inverse problems that include transform domain sparsity regularization.

The following is an example of a linear inverse problem:

$$y = Au + n \quad (1);$$

where $A \in \mathbb{C}^{M \times N}$ is a known encoding operator that is typically ill-conditioned in some sense (e.g., either M<N or it has a bad condition number). Example applications include magnetic resonance imaging ("MRI") reconstruction, computed tomography ("CT") reconstruction, image inpainting, image deblurring, and so on.

An estimate for u can be obtained based on the observations, y, and the encoding matrix, A, by solving, $$\operatorname*{argmin}_{x} dist(y, Ax) + R(x); \quad (2)$$

where dist (•, •) is a distance metric based on the distribution of n and R(x) is a regularizer. Usually, n is representative of Gaussian noise, so the distance metric can become $dist(y, Ax) = \|y - Ax\|_2^2$.

A solution for this problem can be obtained by unrolling the optimization procedure that alternates between a data consistency unit and a regularizer unit. This unrolled machine learning algorithm (e.g., an unrolled neural network) can then be trained end-to-end.

An example for MRI is described below, but it will be appreciated that the systems and methods described in the present disclosure can be adapted for training ML algorithms for solving inverse problems in other applications, including image reconstruction in other imaging modalities.

Figure 1B:
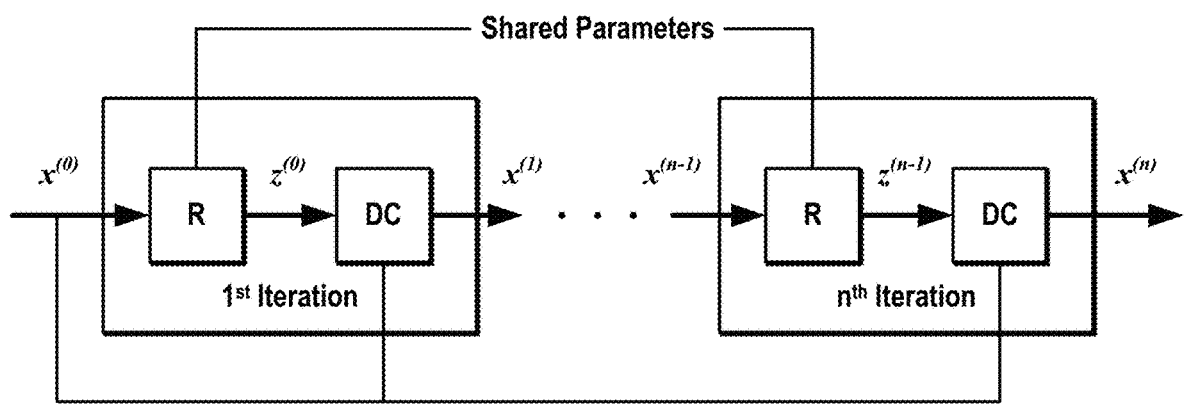
FIG. 1B shows an unrolled neural network architecture with each step including a regularization (R) and a data consistency (DC) unit.

As a non-limiting example, a physics-based deep learning ("DL") MRI reconstruction is now described. Let $y_\Omega$ be the acquired data in k-space, where $\Omega$ denotes the sub-sampling pattern of acquired locations, and let x be the image to be recovered. The forward model for this problem is, $$y_\Omega = E_\Omega x + n \quad (3);$$

where $E_\Omega : \mathbb{C}^{M \times N} \to \mathbb{C}^P$ is the forward encoding operator, which in this example includes a partial Fourier matrix and the sensitivities of the receiver coil array, and $n \in \mathbb{C}^P$ is the measurement noise. Eqn. (3) is generally ill-posed and thus commonly solved using a regularized least squares problem, such as the following, $$\operatorname*{argmin}_{x} \|y_\Omega - E_\Omega x\|_2^2 + R(x); \quad (4)$$

where the first term enforces data consistency with acquired measurements, and R (•••) is a regularizer. As noted above, in some implementations the inverse problem may be a compressed sensing based reconstruction, or other inverse problem that include a transform domain sparsity regularization. As a non-limiting example, the regularizer in these instances may have a form similar to $\lambda \|\Psi x\|_1$, where $\lambda$ is a regularization parameter and $\Psi$ is a sparsifying transform, such as a wavelet transform. Some examples of existing techniques to solve the optimization problem in Eqn. (4) include alternating between enforcing data consistency with acquired data $y_\Omega$ and a proximal operation involving R(•••). For instance, using variable-splitting yields the following:

$$z^{(i-1)} = \operatorname*{argmin}_{z} \mu \|x^{(i-1)} - z\|_2^2 + R(z); \quad (5)$$

$$x^{(i)} = \operatorname*{argmin}_{x} \|y_\Omega - E_\Omega x\|_2^2 + \mu \|x - z^{(i-1)}\|; \quad (6)$$

where $z^{(i)}$ is an intermediate variable, $x^{(i)}$ is the desired image (i.e., the network output) at the ith iteration, and $\mu$ is a penalty parameter, which as one example may be a quadratic penalty parameter. As a non-limiting example, the algorithm can be initialized with the initial image, $x^{(0)}$, being obtained from zero-filled undersampled k-space data. This algorithm can be unrolled for a fixed number of iterations, leading to the process shown in FIGS. 1A-1C. FIG. 1A shows the iterative scheme of a reconstruction problem. FIG. 1B shows an unrolled neural network architecture with each step including a regularization ("R") unit and a data consistency ("DC") unit. As an example, the regularization unit can be a trainable unit with convolutional neural networks to proxy the regularization update at the sub-problem in Eqn. (5) and the data consistency unit can be a linear unit to enforce the data consistency by solving the sub-problem in Eqn. (6).

Figure 1C:
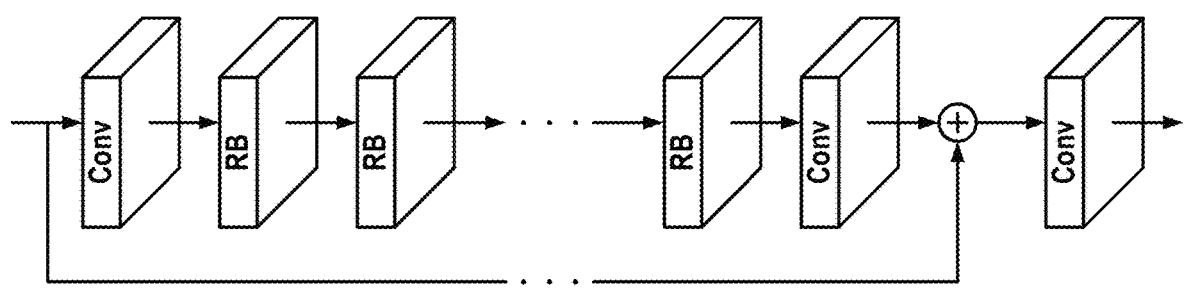
FIG. 1C shows an example of a ResNet architecture containing convolutional layers and residual blocks (RB) which include two convolutional layers with the first one being followed by a ReLU and the second one being followed by a constant multiplication layer.

FIG. 1C shows an example of a ResNet architecture containing convolutional layers and residual blocks ("RB"). Each residual block can include two convolutional layers with the first convolutional layer being followed by a rectified linear unit ("ReLU") or other suitable activation layer, and the second convolutional later being followed by a constant multiplication layer. Although parameter sharing is shown in the network architecture in FIG. 1C, it will be appreciated that in other implementations parameter sharing may not be implemented.

Physics-based DL-MRI methods train this unrolled algorithm end-to-end using fully-sampled training datasets. The sub-problem in Eqn. (5) is typically implemented by means of a convolutional neural network ("CNN"), while the data-consistency sub-problem in Eqn. (6) is typically solved via, $$x^{(i)} = (E_\Omega^H E_\Omega + \mu I)^{-1} (E_\Omega^H y_\Omega + \mu z^{(i-1)}) \quad (7);$$

where I is the identity matrix and $(\cdots)^H$ is the Hermitian operator. Eqn. (7) can be solved via conjugate gradient to avoid matrix inversion. The unrolled network is then trained end-to-end, either by allowing different parameters for each iteration or by sharing all trainable parameters across iterations.

In the supervised setting, images generated from fully-sampled data are often utilized as ground truth for training. As an example, let $x_{ref}^i$ denote the ground truth image for a subject, i. Let $f(y_\Omega^i, E_\Omega^i; \theta)$ denote the output of the unrolled network for the sub-sampled k-space data, $y_\Omega^i$, and encoding matrix, $E_\Omega^i$, of the ith subject, where the network is parameterized by $\theta$. These parameters are learnt using, $$\min_{\theta} \sum_{i=1}^{N} L(x_{ref}^i, f(y_\Omega^i, E_\Omega^i; \theta)); \quad (8)$$

where N is the number of fully-sampled datasets in the training database, and L (•,•) is a loss function between the output image of the network and the reference image. The loss function may be an $l_2$ norm, an $l_1$ norm, a mixed norm, a perception based loss, or other suitable loss function.

As discussed above, there are several scenarios where fully-sampled data cannot be acquired. The systems and methods described in the present disclosure address and overcome this problem by dividing the acquired sub-sampled data indices, $\Omega$, into two sets: $\Theta$ and $\Lambda$, as, $$\Omega = \Theta \cap \Lambda \qquad (9);$$

where $\Theta$ denotes a set of k-space (or other data) locations used within the network during training, and $\Lambda$ denotes a set of k-space (or other data) locations used in the loss function. As indicated in Eqn. (9), the data subsets $\Theta$ and $\Lambda$ may be disjoint sets. Training can be performed using the forward operator (e.g., the encoding matrix) in the training for data consistency. In applications other than MRI applications, $\Omega = \{1, 2, \ldots, M\}$ can represent the rows of the encoding matrix, which may be represented as A or $E_\Omega$. The loss criterion set, $\Lambda$, can be selected as a subset of $\Omega$ by selecting some rows of A or $E_\Omega$ and not using them during training.

In the absence of reference fully-sampled datasets, a loss function of the following form can be minimized:

$$\min_\theta \frac{1}{N} \sum_{i=1}^{N} L(y_\Lambda^i, E_\Lambda^i f(y_\Theta^i, E_\Theta^i; \theta)). \qquad (10)$$

The loss function can be defined between the network output image and a vector of k-space (or other data) points, unlike in the supervised case, which traditionally has a loss function defined over the image domain only. It is contemplated that by performing the loss on the loss criterion set instead of the whole acquired data, the network can be better-suited to avoid over-fitting issues and can therefore generalize to test dataset.

Unlike a supervised approach, only a subset of measurements, $\Theta$, is used as input to the unrolled network. The network output can be transformed to k-space, where the loss is performed only at unseen k-space indices, $\Lambda$. After training is completed, testing can be performed on the unseen dataset using all available measurements, $\neq$.

In some implementations, a generative adversarial network ("GAN") may be implemented. In such instances, more than one loss function may be used. For example, one loss function may be used for the generator portion of the GAN and one loss function may be used for the discriminator portion of the GAN. One or both of these loss functions could be adapted as described in the present disclosure to make use of sub-sampled data sets that are individually separated into training and loss criterion data.

In one non-limiting example, training was performed end-to-end by unrolling the algorithm for 10 iterations, where each iteration included regularization and data consistency units. The regularization CNN employed in this example was a ResNet structure, which included a layer of input and output convolution layers and 15 residual blocks (RB) with skip connections that facilitated the information flow during the network training. Each RB included two convolutional layers, in which first layer was followed by a rectified linear unit (ReLU) and the second layer was followed by a constant multiplication layer. All layers had a kernel size of 3×3, 64 channels. The data consistency unit used a conjugate gradient approach, which itself was unrolled for 10 iterations. Coil sensitivity maps in the encoding matrices were generated using ESPIRiT. The whole network had a total of 592,129 trainable parameters. A normalized $\ell_1 - \ell_2$ loss, defined as, $$L(u, v) = \frac{\|u - v\|_2}{\|u\|_2} + \frac{\|u - v\|_1}{\|v\|_1}; \qquad (11)$$

was used for the self-supervised training. For the self-supervised setting, $\Theta$ was chosen as $\Omega/\Lambda$. The networks were trained using an Adam optimizer with a learning rate of $10^{-3}$ by minimizing the respective loss functions, and a batch size of 1 over 100 epochs.

In an example study, coronal proton density weighted knee MRI data were used for training and testing. Training data included 300 slices from 10 patients. Each raw k-space data was of size 320×368×15 where the first two dimensions are the matrix sizes and the last dimension is the number of coils. Testing was performed on 380 slices collected from 10 subjects.

The fully sampled raw data were undersampled retrospectively using a uniform sub-sampling pattern with an acceleration rate of 4, and 24 lines as autocalibrated signal ("ACS") data.

In the first set of experiments, the effect of the choice of $\Lambda$ on the proposed self-supervised training was evaluated. Because $\Lambda$ is a retrospectively selected subset of $\Omega$ during reconstruction, its choice is not constrained by physical limitations, such as gradient switching. Thus, $\Lambda$ can be selected among all possible k-space locations in $\Omega$. In some implementations, a uniformly random selection of $\Lambda$ can be used. In other instances, a variable-density selection of $\Lambda$, such as a variable-density selection based on Gaussian weighting, can be used. Subsequently, the cardinality of $\Lambda$ was varied among $\{0.05, 0.1, 0.2, 0.3, 0.4\}$ of the cardinality of $\Omega$. For these different values of $|\Lambda|/|\Omega| \in \{0.05, 0.1, 0.2, 0.3, 0.4\}$, it was observed that residual artifacts decreased as the ratio of $|\Lambda|/|\Omega|$ increased, and were effectively eliminated for $|\Lambda|/|\Omega| \in \{0.3, 0.4\}$. Quantitative results indicated that these two values had similar performance, with the latter showing slightly more visual improvement. Based on this example study, it is contemplated that a variable-density selection with sufficient cardinality is advantageous.

Thus, a self-supervised training method for physics-driven inverse problem reconstructions in the absence of full-sampled data has been described. Sub-sampled data indices $\Omega$ were divided into two sets: $\Theta$ and $\Lambda$, where the former was used during data consistency in the unrolled network and the latter was utilized in the loss function. The systems and methods described in the present disclosure can be advantageous for training a reconstruction algorithm that removes aliasing artifacts, achieving comparable performance to the conventional supervised learning approach that has access to fully-sampled data, while outperforming traditional compressed sensing or parallel imaging reconstructions.

In many scenarios, acquisition of fully-sampled data is challenging due to physiological and physical constraints. The lack of ground truth data hinders the utility of the supervised learning approaches in these scenarios. The proposed self-supervised approach relies only on available sub-sampled measurements. While the example described above relates to MRI reconstruction, it is again noted that the proposed approach naturally extends to other linear inverse problems, and has potential applications in other imaging modalities. Additionally or alternatively, machine learning algorithms can be trained as described in the present disclosure for application of nonlinear inverse problems.

Figure 2:
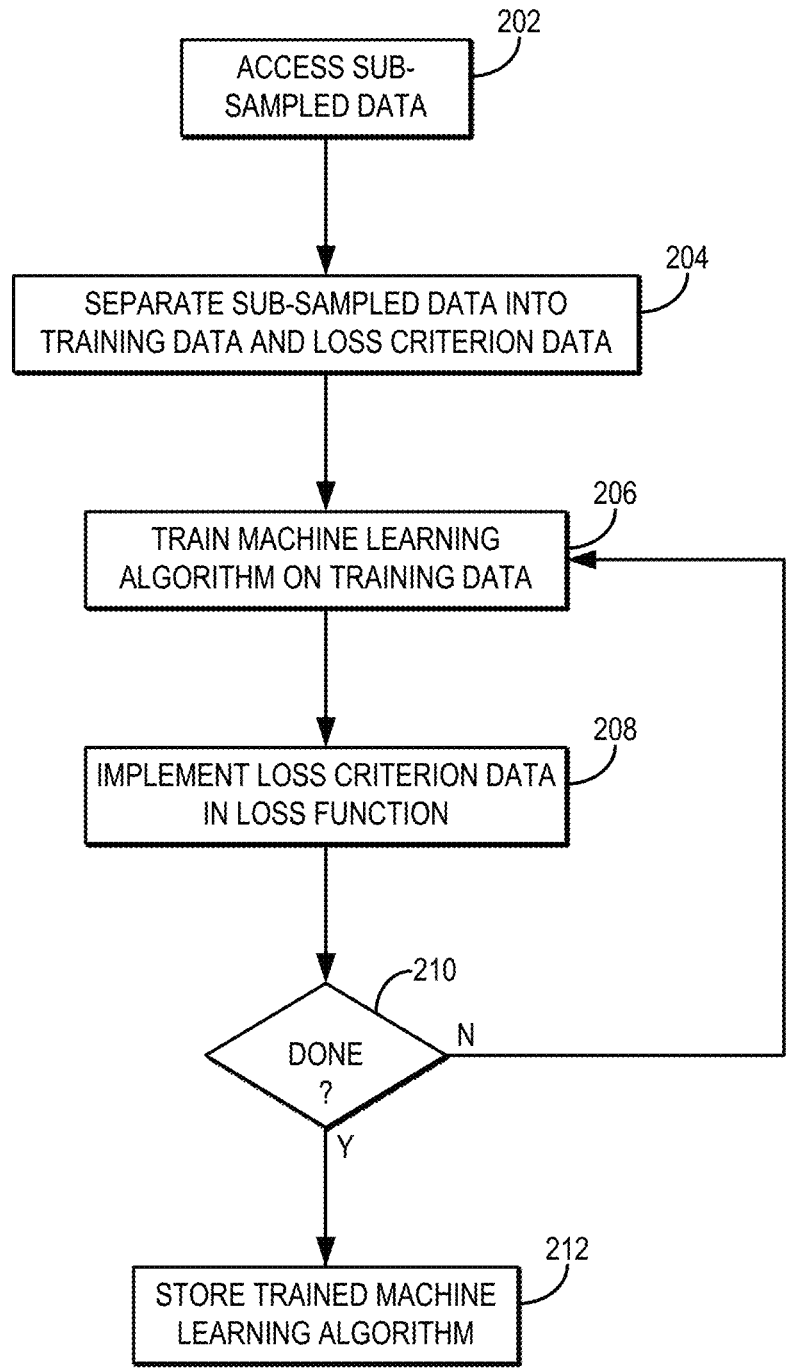
FIG. 2 is a flowchart setting forth the steps of an example method for training and implementing a machine learning algorithm, in which a sub-sampled data set is separated into training data for training the machine learning algorithm to implement an inverse problem and loss criterion data that are otherwise utilized in implementing a loss function.

Referring now to FIG. 2, a flowchart is illustrated as setting forth the steps of an example method for training and implementing a machine learning algorithm, in which a sub-sampled data set is separated into training data for training the machine learning algorithm to implement an inverse problem and loss criterion data that are otherwise utilized in implementing a loss function.

The method includes accessing sub-sampled data with a computer system, as indicated at step 202. Accessing the sub-sampled data can include retrieving such data from a database, a memory, or other suitable data storage device or medium. In other instances, the sub-sampled data can be scan-specific data, in which the sub-sampled data are acquired from a subject and communicated or otherwise transferred to the computer system. In these instances, the sub-sampled data can be acquired using a suitable imaging, sensor, or measurement system. As one example, the sub-sampled data can be acquired using a medical imaging system, such as an MRI system or a CT system. In other examples, the sub-sampled data may be acquired with another imaging system, such as a crystallography system and/or a microscopy system. In these instances, the sub-sampled data may instead be ill-conditioned data, or otherwise non-invertible data.

The sub-sampled data are then separated into a first subset of data for training a machine learning algorithm and a second subset of data that is utilized in a loss function used when training the machine learning algorithm, as indicated at step 204. The first subset of data can therefore be referred to as training data and the second subset of data can be referred to as loss criterion data.

The machine learning algorithm is then trained on the training data, as indicated at step 206. Training the machine learning algorithm can include using the training data to enforce data consistency using a forward model, such as by enforcing consistency of an estimate with the training data using the forward model. Training the machine learning algorithm utilizes a loss function, which as noted above implements the loss criterion data, as indicated at step 208. These steps can occur serially or in parallel. As one example, the machine learning algorithm can be an artificial neural network, such as a convolutional neural network, a residual neural network, or so on. The machine learning algorithm may in some instances be an unrolled machine learning algorithm. As described above, training the machine learning algorithm can include incorporating the forward operator (e.g., the encoding matrix) into the training process. As described above, the machine learning algorithm can be trained on the training data using, in part, a loss function that implements the separate subset of loss criterion data.

As one example, training a neural network may include initializing the neural network, such as by computing, estimating, or otherwise selecting initial network parameters (e.g., weights, biases, or both). Training data can then be input to the initialized neural network, generating output as output data, which in the context of an image reconstruction technique can include one or more reconstructed images. The quality of the output data can then be evaluated, such as by passing the output data to the loss function to compute an error. The current neural network can then be updated based on the calculated error (e.g., using backpropagation methods based on the calculated error). For instance, the current neural network can be updated by updating the network parameters (e.g., weights, biases, or both) in order to minimize the loss according to the loss function. When the error has been minimized (e.g., by determining whether an error threshold or other stopping criterion has been satisfied), the current neural network and its associated network parameters represent the trained neural network.

When training of the machine learning algorithm is completed, as determined at decision block 210, the trained machine learning algorithm is stored for later use, as indicated at step 212. In some instances, training can conclude after a stopping criterion has been satisfied. In some other instances, training can conclude after a preset number of iterations. Storing the neural network(s) may include storing network parameters (e.g., weights, biases, or both), which have been computed or otherwise estimated by training the neural network(s) on the training data. Storing the trained neural network(s) may also include storing the particular neural network architecture to be implemented. For instance, data pertaining to the layers in the neural network architecture (e.g., number of layers, type of layers, ordering of layers, connections between layers, hyperparameters for layers) may be stored.

The trained machine learning algorithm can then be retrieved for use, such as to reconstruct images or in other linear inverse problem or nonlinear inverse problem applications.

Figure 3:
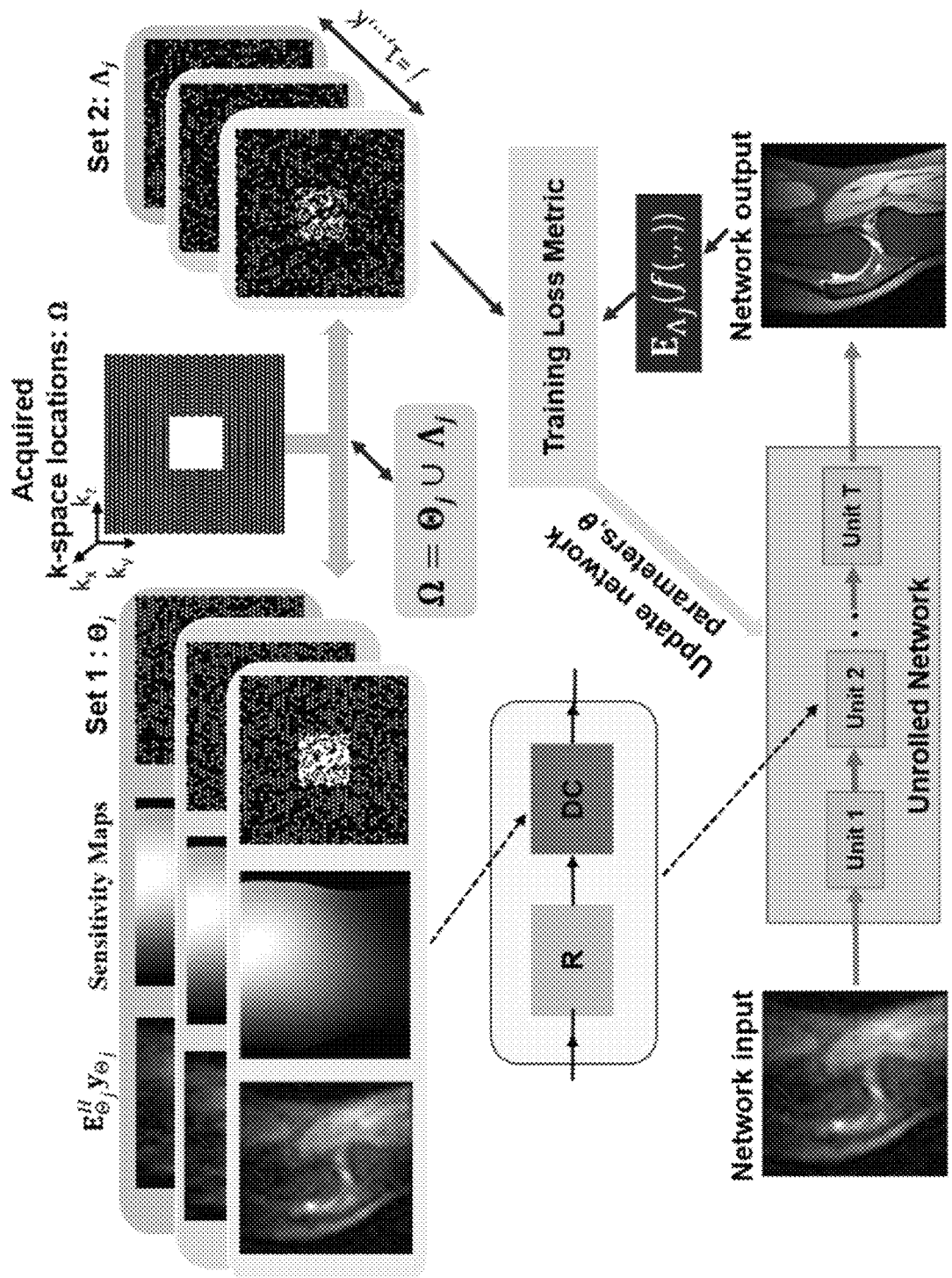
FIG. 3 shows a multi-mask self-supervised learning scheme to train physics-guided deep learning without fully-sampled data. The acquired sub-sampled k-space measurements for each scan, D., are split into multiple disjoint sets, $\Theta_j$ and $\Lambda_j$ in which $\Omega = \Theta_j \cup \Lambda_j$, for $j \in \{1, \ldots, K\}$. The first set of indices, $\Theta_j$, is used in the data consistency unit of the unrolled network, while the latter set, $\Lambda_j$ is used to define the loss function for training. During training, the output of the network is transformed to k-space, and the available subset of measurements at $\Lambda_j$ are compared with the corresponding reconstructed k-space values. Based on this training loss, the network parameters are subsequently updated.

In some implementations, multiple masks can be used in order to further improve the reconstruction performance of the self-supervised learning via data undersampling ("SSDU") systems and methods described in the present disclosure. SSDU reconstruction quality may degrade at very high acceleration rates due to higher data scarcity, arising from the splitting of $\Omega$ into $\Theta$ and $\Lambda$. The multi-mask implementation of SSDU addresses these situations by splitting the acquired measurements, $\Omega$, into multiple pairs of disjoint sets for each training slice, while using one of these sets for DC units and the other for defining loss, similar to the SSDU techniques described above. The multi-mask SSDU approach can significantly improve upon SSDU performance at high acceleration rates, in addition to providing SNR improvement and aliasing artifact reduction relative to other deep learning-based MRI reconstruction techniques. An example workflow for the multi-mask SSDU approach is shown in FIG. 3.

In general, the available measurements are split multiple times for each subject i, such that for each partition $\Omega = \Theta_j \cup \Lambda_j$ for j=1, ... ,K denoting the number of partitions for each scan. Similar to the SSDU techniques described above, each pair of sets in each scan can be disjoint; that is, $\Lambda_j = \Omega \backslash \Theta_j$ for j∈{1, ... ,K}. Hence, the following loss function can be minimized during training:

$$\min_{\theta} \frac{1}{N \cdot K} \sum_{i=1}^{N} \sum_{j=1}^{K} L\left(y^i_{\Lambda_j}, E^i_{\Lambda_j}\left(f\left(y^i_{\Theta_j}, E^i_{\Theta_j}; \theta\right)\right)\right). \tag{12}$$

This multi-mask approach enables efficient usage of available data by ensuring a higher fraction of low and high frequency components are utilized in training and loss masks.

There are several tunable hyperparameters in the multi-mask SSDU implementation, including the number of partitions, K in Eqn. (12), as well as the distribution and size of $\Lambda$. As one non-limiting example, a variable-density Gaussian distribution can be used for $\Lambda$, such as may be used for a single mask. As another non-limiting example, a uniformly random distribution can be used. In an example implementation, the size of Λ can be optimized to ρ=0.4. It will be appreciated that the size of Λ may be set to values other than ρ=0.4, which may be determined in part based on the distribution used for Λ. After these two hyperparameters are set, the number of partitions of each scan, K, can be varied (e.g., among 3, 5, 6, 7, 8 and 10) to optimize the remaining distinct hyperparameters of the multi-mask SSDU. In some implementations, a random selection of masks can be used. As another example, a cyclic selection of masks may be used, which may ensure that all acquired measurements are used for both training and loss.

As a non-limiting example, the iterative optimization problem in Eqns. (5) and (6) can be unrolled for a selected number of iterations, such as T=10 iterations. Conjugate gradient descent can be used in the DC units of the unrolled network. Similar to the examples described above, a ResNet structure can be used for the regularizer in Eqn. (5), and the network parameters can be shared across the unrolled network. Coil sensitivity maps can be generated, for instance, from a 24×24 center of k-space using ESPIRiT or other suitable techniques.

As a pre-processing step in some implementations, the maximum absolute value of the k-space datasets can be normalized to 1 in all cases. The networks can be trained using an Adam optimizer with a learning rate of $5 \times 10^{-4}$ by minimizing the normalized $\ell_1 - \ell_2$ loss function with a batch size of 1 over 100 epochs.

In this way, the self-supervision via data undersampling techniques described in the present disclosure, which train physics-guided neural networks without fully-sampled data, can be adapted to a multi-mask setting where multiple pairs of disjoint sets are used for each training slice in the dataset. This multi-mask SSDU implementation further improves SSDU training by more efficiently utilizing the acquired data via multiple masking operations. As one advantage, this can suppress residual artifacts that may otherwise be seen in networks trained using single-mask SSDU implementations.

The multi-mask SSDU techniques described in the present disclosure can advantageously be implemented as an alternative technique for data augmentation in DL-MRI reconstruction. Conventional data augmentation techniques such as rotations are not well-suited for conventional DL-MRI reconstructions due to the way the rotations modify the undersampled k-space data. With the multi-mask data augmentation provided by the techniques described in the present disclosure, self-supervised training can be rated higher than supervised training in terms of noise and aliasing artifacts.

Figure 4:
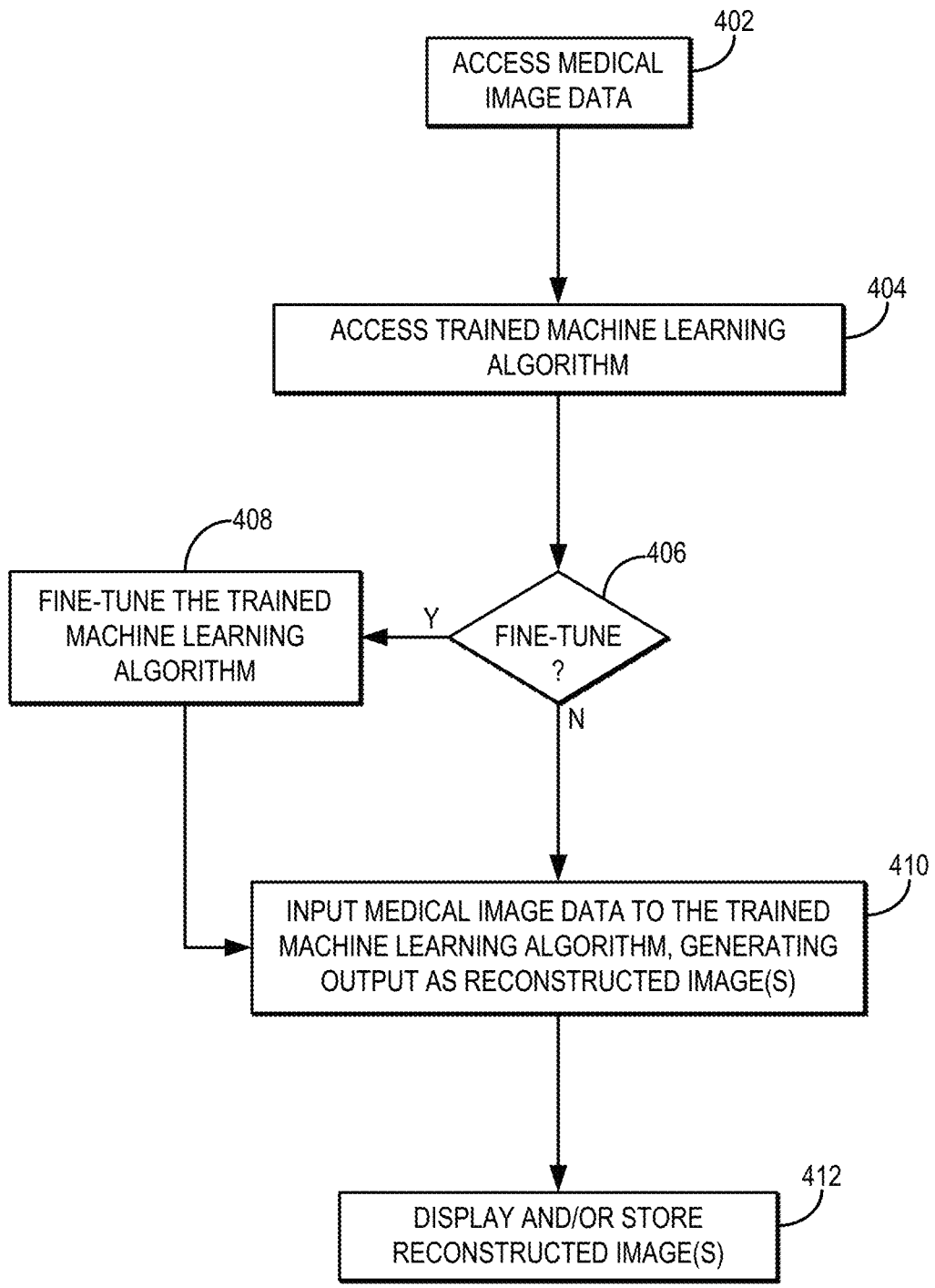
FIG. 4 is a flowchart setting forth the steps of an example method for implementing a pre-trained neural network or other machine learning algorithm to reconstruct images from undersampled medical image data, where the neural network or other machine learning algorithm has been trained in accordance with the methods described in the present disclosure.

Referring now to FIG. 4, a flowchart is illustrated as setting forth the steps of an example method for reconstructing an image from undersampled k-space data using a suitably trained neural network or other machine learning algorithm.

The method includes accessing medical image data with a computer system, as indicated at step 402. The medical image data generally include measurement data acquired with a medical imaging system. For instance, the medical image data may include k-space data acquired with an MRI system, sinogram data acquired with a CT system, and so on. Advantageously, the medical image data are undersampled data. In general, medical image data can be undersampled when the sampled data points contained in the medical image data do not satisfy the Nyquist criterion.

Accessing the medical image data may include retrieving such data from a memory or other suitable data storage device or medium. Alternatively, accessing the medical image data may include acquiring such data with a medical imaging system and transferring or otherwise communicating the data to the computer system, which may be a part of the medical imaging system.

In some embodiments, the medical image data are undersampled k-space data acquired with an MRI system. For instance, the k-space data can be undersampled by an acceleration factor of R=2, R=4, R=6, R=8, or other suitable acceleration factor. The k-space data can be uniformly undersampled, or non-uniformly undersampled. As one non-limiting example, the k-space data can be undersampled with an acceleration factor of R=8 using a sheared uniform $k_y - k_z$ undersampling pattern. Other undersampling patterns may also be used.

A trained neural network (or other suitable machine learning algorithm) is then accessed with the computer system, as indicated at step 404. In general, the neural network is trained, or has been trained, using the techniques described above in order to reconstruct images from undersampled medical image data, such as undersampled k-space data.

Accessing the trained neural network may include accessing network parameters (e.g., weights, biases, or both) that have been optimized or otherwise estimated by training the neural network on training data. In some instances, retrieving the neural network can also include retrieving, constructing, or otherwise accessing the particular neural network architecture to be implemented. For instance, data pertaining to the layers in the neural network architecture (e.g., number of layers, type of layers, ordering of layers, connections between layers, hyperparameters for layers) may be retrieved, selected, constructed, or otherwise accessed.

In some implementations, the pre-trained neural network, or other machine learning algorithm, can be fine-tuned in a scan-specific manner using transfer learning. All of the layers in the pre-trained network can be fine-tuned, or alternatively only a subset of the layers can be fine-tuned (e.g., only higher-level portions/earlier layers of the pre-trained network can be fine-tuned).

A determination is thus made at decision block 406 whether the pre-trained neural network or other machine learning algorithm should be fine-tuned. If so, then, as indicated at step 408, the pre-trained neural network or other machine learning algorithm parameters are fine-tuned in a scan-specific (i.e., subject-specific) manner using the undersampled medical image data accessed at step 402. Advantageously, fine-tuning the pre-trained network in this manner can further improve reconstruction performance. Based on the techniques described in the present disclosure, a pre-trained network can be fine-tuned (e.g., on a per-scan or scan-specific basis) using the following loss function for the fine-tuning phase:

$$\min_\theta L(y_\Lambda, E_\Lambda(f(y_\Theta, E_\Theta; \theta))); \quad (13)$$

where $E_\Lambda$ transforms the network output image into the k-space domain (e.g., the coil k-space domain), so the loss can be defined with respect to the k-space points $y_\Lambda$. The network parameters θ can be initialized with the database-trained network values. These parameters are then fine-tuned, using only the same data that are to be reconstructed, such that the fine tuning of the network is performed on a per-scan or scan-specific basis. Thus, $y_\Theta$ is used as the data input to the neural network, whose parameters are tuned to best estimate $y_\Lambda$ at the output based on the loss function.

During the final reconstruction, the complete set of measurement data $y_\Omega$ is then input into the finely-tuned network.

The medical image data are then input to the neural network or other machine learning algorithm, whether fine-tuned or otherwise accessed, generating output as one or more reconstructed images, as indicated at step 410. The image(s) generated by inputting the medical image data to the trained neural network(s) can then be displayed to a user, stored for later use or further processing, or both, as indicated at step 412.

Figure 5:
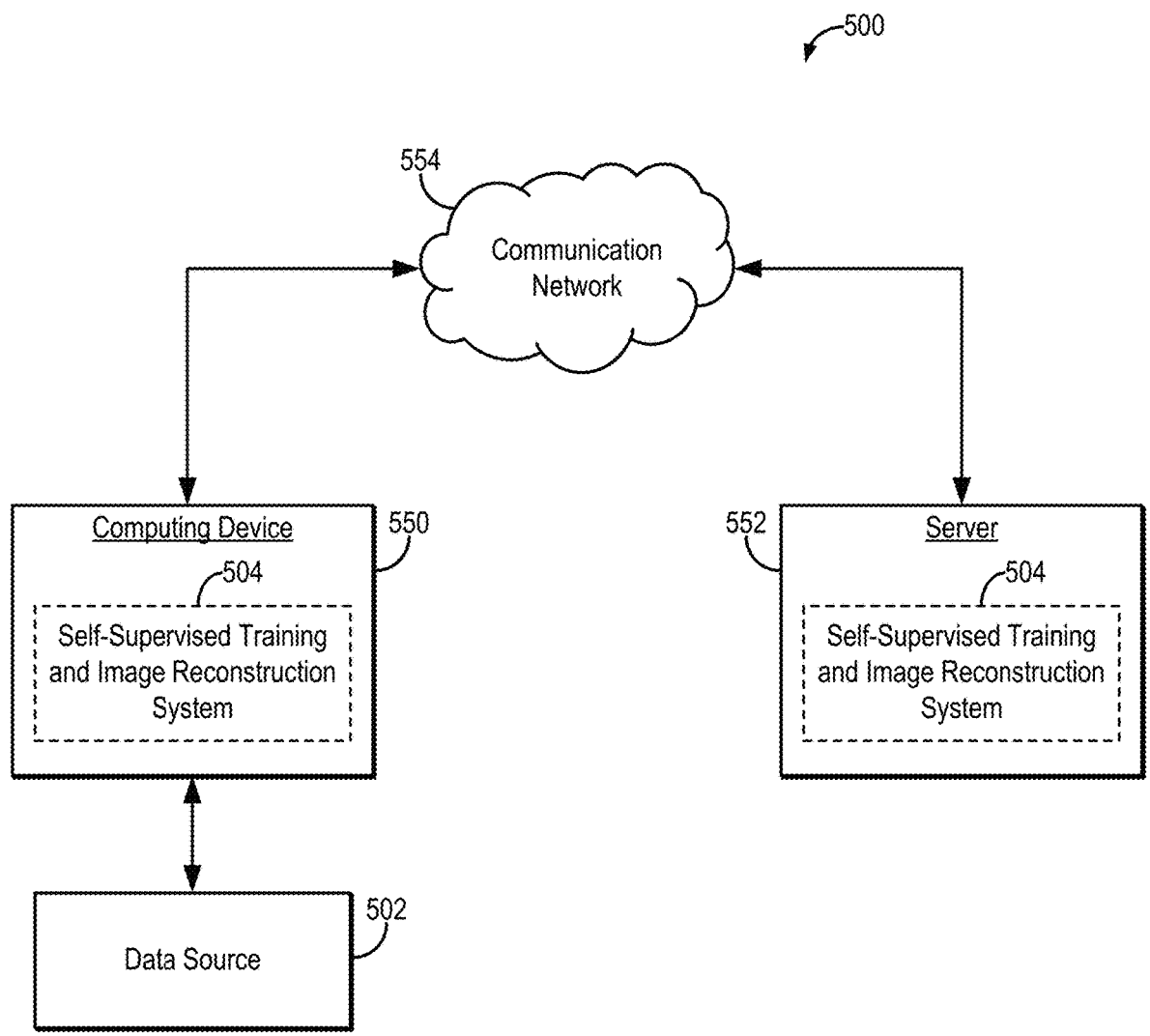
FIG. 5 is a block diagram of an example self-supervised training and image reconstruction system that can implement the methods described in the present disclosure.

Referring now to FIG. 5, an example of a system 500 for training and implementing a machine learning algorithm to reconstruct an image in accordance with some embodiments of the systems and methods described in the present disclosure is shown. As shown in FIG. 5, a computing device 550 can receive one or more types of data (e.g., k-space data, sinogram data, other image data or sub-sampled data) from data source 502, which may be a medical image data source. In some embodiments, computing device 550 can execute at least a portion of a self-supervised training and image reconstruction system 504 to train and implement a machine learning algorithm to reconstruct an image from data received from the data source 502.

Additionally or alternatively, in some embodiments, the computing device 550 can communicate information about data received from the data source 502 to a server 552 over a communication network 554, which can execute at least a portion of the self-supervised training and image reconstruction system 504. In such embodiments, the server 552 can return information to the computing device 550 (and/or any other suitable computing device) indicative of an output of the self-supervised training and image reconstruction system 504.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552 can also reconstruct images from the data.

In some embodiments, data source 502 can be any suitable source of image data (e.g., measurement data, images reconstructed from measurement data), such as an MRI system, a CT system, another medical imaging system, another computing device (e.g., a server storing image data), and so on. In some embodiments, data source 502 can be local to computing device 550. For example, data source 502 can be incorporated with computing device 550 (e.g., computing device 550 can be configured as part of a device for capturing, scanning, and/or storing images). As another example, data source 502 can be connected to computing device 550 by a cable, a direct wireless link, and so on. Additionally or alternatively, in some embodiments, data source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 554 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
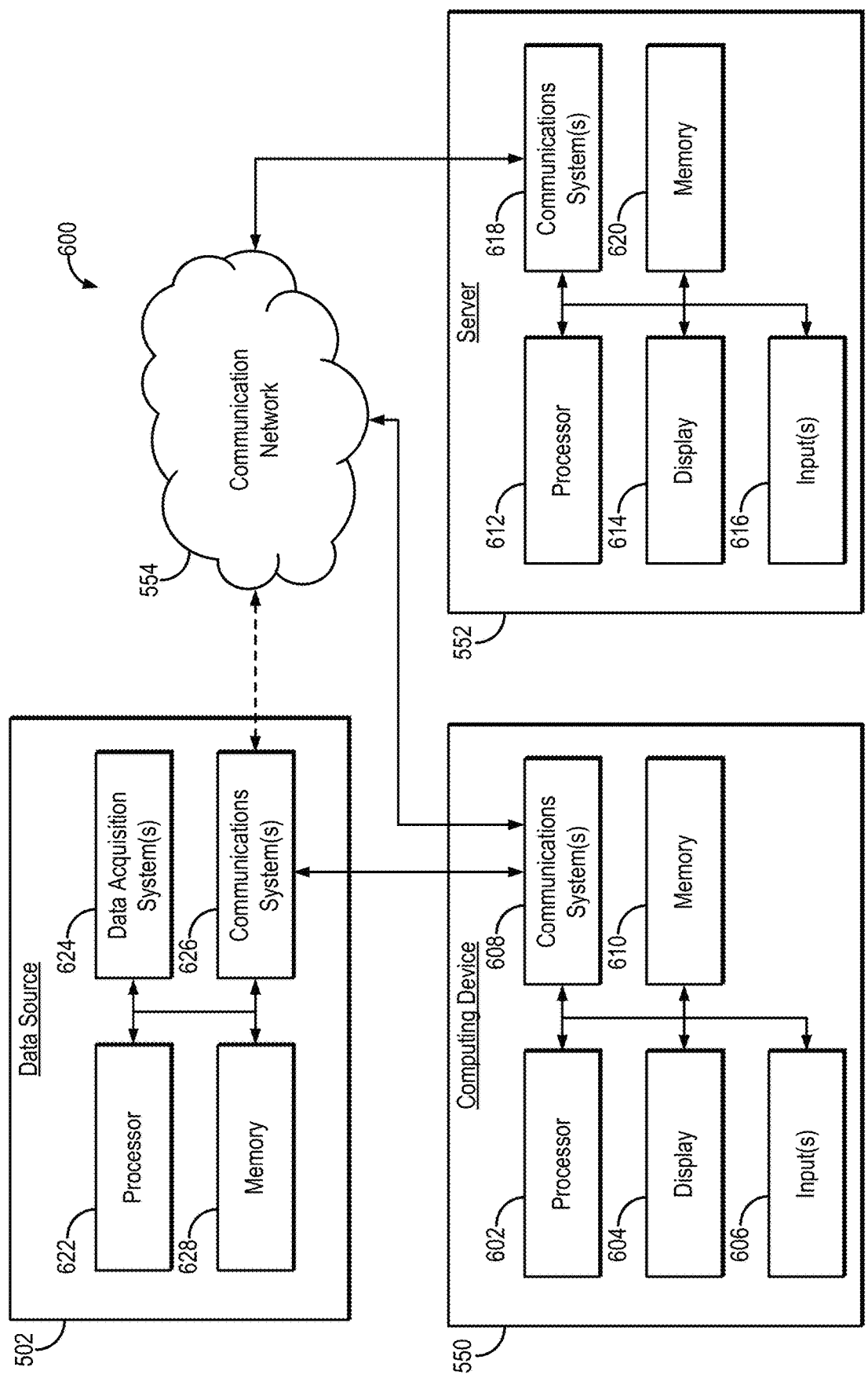
FIG. 6 is a block diagram of example components that can implement the system of FIG. 5.

Referring now to FIG. 6, an example of hardware 600 that can be used to implement data source 502, computing device 550, and server 552 in accordance with some embodiments of the systems and methods described in the present disclosure is shown. As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. In some embodiments, display 604 can include any suitable display devices, such as a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display 604, to communicate with server 552 via communications system(s) 608, and so on. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on.

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, data source 502 can include a processor 622, one or more data acquisition systems 624, one or more communications systems 626, and/or memory 628. In some embodiments, processor 622 can be any suitable hardware processor or combination of processors, such as a CPU, a GPU, and so on. In some embodiments, the one or more data acquisition systems 624 are generally configured to acquire data, images, or both, and can include an MRI system, a CT system, another medical imaging system, and so on. Additionally or alternatively, in some embodiments, one or more data acquisition systems 624 can include any suitable hardware, firmware, and/or software for coupling to and/or controlling operations of an MRI system, a CT system, another medical imaging system, or so on. In some embodiments, one or more portions of the one or more data acquisition systems 624 can be removable and/or replaceable.

Note that, although not shown, data source 502 can include any suitable inputs and/or outputs. For example, data source 502 can include input devices and/or sensors that can be used to receive user input, such as a keyboard, a mouse, a touchscreen, a microphone, a trackpad, a trackball, and so on. As another example, data source 502 can include any suitable display devices, such as a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more data acquisition systems 624, and/or receive data from the one or more data acquisition systems 624; to images from data; present content (e.g., images, a user interface) using a display; communicate with one or more computing devices 550; and so on. Memory 628 can include any suitable volatile memory, non-volatile memory, storage, or any suitable combination thereof. For example, memory 628 can include RAM, ROM, EEPROM, one or more flash drives, one or more hard disks, one or more solid state drives, one or more optical drives, and so on. In some embodiments, memory 628 can have encoded thereon, or otherwise stored therein, a program for controlling operation of data source 502. In such embodiments, processor 622 can execute at least a portion of the program to generate images, transmit information and/or content (e.g., data, images) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A computer-implemented method for training a machine learning algorithm to reconstruct an image, the method comprising:
   accessing sub-sampled data with a computer system, wherein the sub-sampled data are k-space data acquired with a magnetic resonance imaging (MRI) system;
   dividing the sub-sampled data into a first k-space data subset and a second k-space data subset using the computer system;
   training a machine learning algorithm by inputting the first k-space data subset to the machine learning algorithm during training to enforce data consistency using a forward model while evaluating a loss function during training of the machine learning algorithm using the second k-space data subset; and storing the trained machine learning algorithm in the computer system for later use.

2. The method of claim 1, wherein the loss function is defined between an output image and the second k-space data subset.

3. The method of claim 2, wherein the second data subset comprises a vector of k-space data points.

4. The method of claim 1, wherein the first k-space data subset is selected such that it comprises a number of elements that is a fraction of a total number of elements in the sub-sampled data.

5. The method of claim 1, wherein the machine learning algorithm comprises a neural network.

6. The method of claim 5, wherein the neural network is a convolutional neural network.

7. The method of claim 6, wherein the convolutional neural network is a residual neural network.

8. The method of claim 5, wherein the neural network is implemented with an unrolled neural network architecture comprising a plurality of steps, each step including a regularization unit and a data consistency unit.

9. The method of claim 1, wherein the sub-sampled data are partitioned into a number of partitions, such that the first k-space data subset comprises a plurality of first k-space data subsets, wherein the plurality of first k-space data subsets comprises a number of first k-space data subsets that is equal to the number of partitions, and the second k-space data subset comprises a plurality of second k-space data subsets, wherein the plurality of second k-space data subsets comprises a number of second k-space data subsets that is equal to the number of partitions.

10. The method of claim 1, further comprising reconstructing an image by accessing image data with the computer system, retrieving the trained machine learning algorithm with the computer system, and inputting the image data to the trained machine learning algorithm, generating output as a reconstructed image.

11. The method of claim 10, further comprising fine-tuning the trained machine learning algorithm using the image data accessed with the computer system.

12. The method of claim 1, further comprising reconstructing an image by retrieving the trained machine learning algorithm with the computer system, and inputting the sub-sampled data to the trained machine learning algorithm, generating output as a reconstructed image.

13. The method of claim 1, wherein the sub-sampled data comprise a database of sub-sampled data and accessing the sub-sampled data includes accessing a set of sub-sampled data from the database.

14. The method of claim 1, wherein training the machine learning algorithm on the first subset of data comprises using a forward operator when training for data consistency.

15. The method of claim 1, wherein the sub-sampled data comprise scan-specific data obtained from the subject.

16. The method of claim 15, further comprising reconstructing an image by retrieving the trained machine learning algorithm with the computer system, and inputting the sub-sampled data to the trained machine learning algorithm, generating output as a reconstructed image.

17. A method for reconstructing an image from undersampled k-space data, the method comprising:

accessing a pre-trained neural network with a computer system, wherein the pre-trained neural network has been trained on sub-sampled k-space data that were divided into a first k-space data subset and a second k-space data subset, wherein the pre-trained neural network was trained on the first k-space data subset while evaluating a loss function using the second k-space data subset during training;

accessing undersampled k-space data with the computer system, wherein the undersampled k-space data were obtained from a subject using a magnetic resonance imaging (MRI) system;

inputting the undersampled k-space data to the pre-trained neural network, generating output as a reconstructed image that depicts the subject; and displaying the image to a user using the computer system.

18. The method of claim 17, wherein the pre-trained neural network is fine-tuned before inputting the undersampled k-space data to the pre-trained neural network, wherein the pre-trained neural network is fine-tuned by:

dividing the undersampled k-space data into a first data subset and a second data subset;

applying the first data subset to the pre-trained neural network, generating output as an output image;

transforming the output image into k-space, generating output as network output k-space data; and minimizing a loss function between the second data subset and the network output k-space data in order to generate fine-tuned network parameters that best estimate the second data subset based on the loss function.

19. A computer-implemented method for training a machine learning algorithm to reconstruct an image, the method comprising:

accessing sub-sampled data with a computer system, wherein the sub-sampled data are k-space data acquired with a magnetic resonance imaging (MRI) system;

dividing the sub-sampled data into at least a first k-space data subset and a second k-space data subset using the computer system;

training a machine learning algorithm by inputting the first k-space data subset to the machine learning algorithm during training to enforce data consistency using a forward model while evaluating a loss function during training of the machine learning algorithm using at least the second k-space data subset; and storing the trained machine learning algorithm in the computer system for later use.

20. The method of claim 19, wherein the sub-sampled data are partitioned into a number of partitions comprising at least the first k-space data subset and the second k-space data subset.

21. The method of claim 20, wherein the sub-sampled data are partitioned into the number of partitions, such that the first k-space data subset comprises a plurality of first k-space data subsets, wherein the plurality of first k-space data subsets comprises a number of first k-space data subsets that is equal to the number of partitions, and the second k-space data subset comprises a plurality of second k-space data subsets, wherein the plurality of second k-space data subsets comprises a number of second k-space data subsets that is equal to the number of partitions.

22. The method of claim 19, wherein the loss function is defined between an output image and at least the second k-space data subset.

23. The method of claim 22, wherein the second k-space data subset comprises a vector of k-space data points.

24. The method of claim 19, wherein the machine learning algorithm comprises a neural network.

25. The method of claim 24, wherein the neural network is implemented with an unrolled neural network architecture comprising a plurality of steps, each step including a regularization unit and a data consistency unit.

26. The method of claim 19, wherein the sub-sampled data comprise a database of sub-sampled data and accessing the sub-sampled data includes accessing a set of sub-sampled data from the database.

27. The method of claim 19, wherein the sub-sampled data comprise scan-specific data obtained from the subject.

28. The method of claim 27, further comprising reconstructing an image by retrieving the trained machine learning algorithm with the computer system, and inputting the sub-sampled data to the trained machine learning algorithm, generating output as a reconstructed image.

* * * * *